(12) United States Patent
Youssef et al.

(10) Patent No.: US 9,732,022 B2
(45) Date of Patent: Aug. 15, 2017

(54) RECOVERY OF MATERIALS FROM A MOTHER LIQUOR RESIDUE

(71) Applicant: SABIC Innovative Plastics IP B.V., Bergen op Zoom (NL)

(72) Inventors: Ahmed Youssef, Mt. Vernon, IN (US); Mohan Khadilkar, Mt. Vernon, IN (US); Martin Oyevaar, Bergen op Zoom (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 18 days.

(21) Appl. No.: 14/064,479

(22) Filed: Oct. 28, 2013

(65) Prior Publication Data

US 2014/0121417 A1    May 1, 2014

Related U.S. Application Data

(60) Provisional application No. 61/719,549, filed on Oct. 29, 2012.

(51) Int. Cl.
  *C07C 37/74* (2006.01)
  *C07C 37/52* (2006.01)
(52) U.S. Cl.
  CPC .............. *C07C 37/74* (2013.01); *C07C 37/52* (2013.01)
(58) Field of Classification Search
  CPC .................................. C07C 37/52; C07C 37/74
  USPC ........................................................ 568/724
  See application file for complete search history.

(56) References Cited

U.S. PATENT DOCUMENTS

| | | | |
|---|---|---|---|
| 3,466,337 A | 9/1969 | Smith et al. | |
| 4,327,229 A | 4/1982 | Mendiratta | |
| 4,766,254 A | 8/1988 | Faler et al. | |
| 4,847,433 A | 7/1989 | Kissinger | |
| 6,133,486 A | 10/2000 | Maas et al. | |
| 6,191,316 B1 * | 2/2001 | Fennhoff et al. | 568/728 |

FOREIGN PATENT DOCUMENTS

| | | | |
|---|---|---|---|
| EP | 0812815 A2 | | 12/1997 |
| WO | WO00/40531 | * | 10/1999 |
| WO | WO2007/044139 | * | 4/2007 |

OTHER PUBLICATIONS

International Search Report for International Application No. PCT/US2013/067270, International Application Filing Date: Oct. 29, 2013, Date of Mailing: Feb. 11, 2014, 5 pages.
Written Opinion for International Application No. PCT/US2013/067270, International Application Filing Date Oct. 29, 2013, Date of Mailing Feb. 11, 2014, 5 pages.

* cited by examiner

*Primary Examiner* — Paul A Zucker
*Assistant Examiner* — Mark Luderer
(74) *Attorney, Agent, or Firm* — Cantor Colburn LLP

(57) ABSTRACT

A process for recovery of materials from a mother liquor residue comprising cracking a mother liquor residue with an aromatic sulfonic acid catalyst to form a cracked product mixture and separating phenol from the cracked product mixture wherein the mother liquor residue results from distillation of a mother liquor resulting from bisphenol A synthesis and isolation.

13 Claims, 1 Drawing Sheet

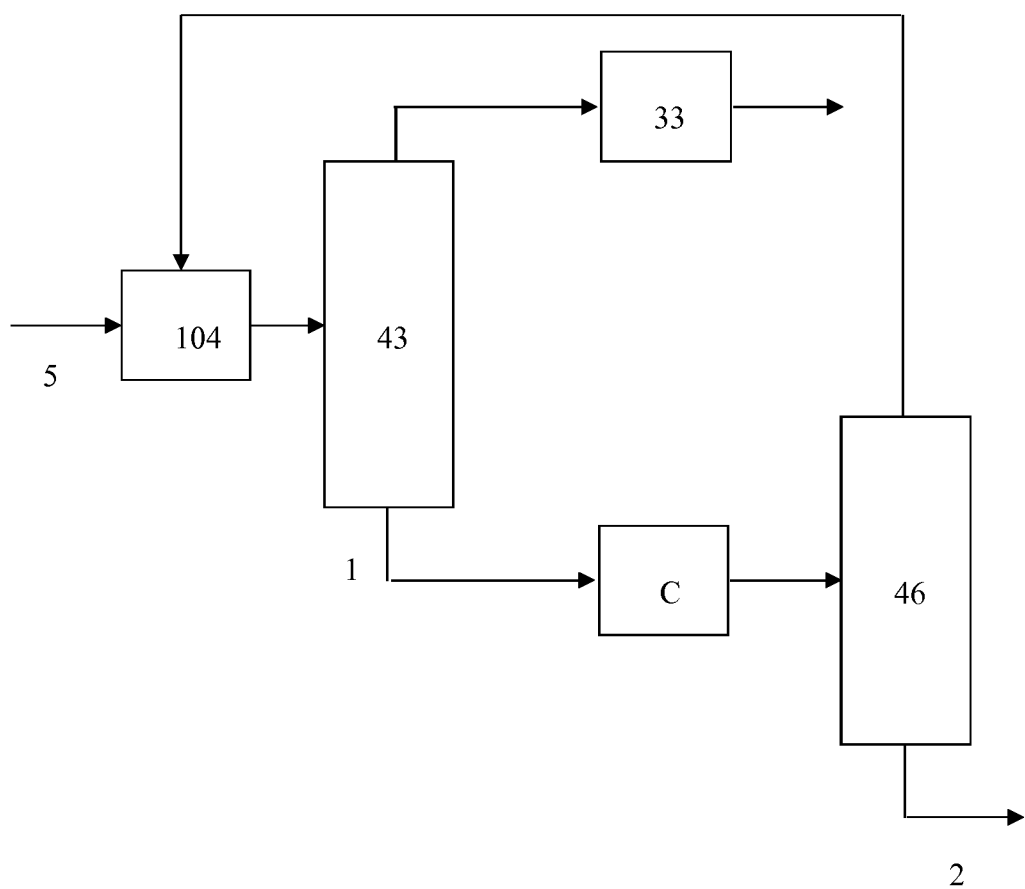

RECOVERY OF MATERIALS FROM A MOTHER LIQUOR RESIDUE

CROSS REFERENCED TO RELATED APPLICATION

This application claims the benefit of U.S. Provisional Patent Application No. 61/719,549 filed on Oct. 29, 2012, and which is hereby incorporated by reference herein in its entirety.

BACKGROUND

Bisphenol A (2,2-bis(4-hydroxyphenyl)propane) is commercially prepared by condensing 2 moles of phenol with a mole of acetone in the presence of an acid catalyst. The phenol is present in a molar excess of the stoichiometric requirement. Currently, the purification of bisphenol A is a costly multi-step procedure entailing distillations, crystallizations, solvent extractions, evaporations and like procedures. Where bisphenol A is separated from the contaminants and purified by crystallization, a mother liquor is obtained. The mother liquor, after distillation, forms a mother liquor residue which contains lower boiling reaction by-products, bisphenol A and higher boiling reaction by-products to name a few components. This mother liquor residue is a tarry residue which still contains valuable, recoverable materials. There exists a need for a method to recover the valuable, recoverable materials from the mother liquor residue.

BRIEF DESCRIPTION

The aforementioned need is addressed by a process for recovery of materials from a mother liquor residue comprising cracking the mother liquor residue with an aromatic sulfonic acid catalyst to form a cracked product mixture and separating phenol from the cracked product mixture wherein the mother liquor residue results from distillation of a mother liquor resulting from bisphenol A synthesis and isolation.

BRIEF DESCRIPTION OF THE DRAWING

Refer now to the figure, which is an exemplary embodiment. FIG. 1 is a schematic representation of an embodiment described herein.

DETAILED DESCRIPTION

As mentioned above bisphenol A is made by the condensation of 2 moles of a phenol with 1 mole of acetone in the presence of an acid catalyst. Phenol is used in excess of the stoichiometric requirements. Exemplary processes are described in U.S. Pat. Nos. 4,766,254, 4,847,433 and 6,133,486, which are incorporated by reference herein in their entirety. The reaction zone effluent is continuously withdrawn and cooled to precipitate crystalline 1:1 adduct of bisphenol A and phenol. The solid adduct is filtered out, leaving a mother liquor. The mother liquor comprises bisphenol A, phenol and by-products.

The mother liquor is treated to recover useful components such as phenol and bisphenol A. For example, the mother liquor can be heated, typically to a temperature of 55° C. to 95° C., to promote isomerization of related isomers of bisphenol A to bisphenol A (2,2-bis(4-hydroxyphenyl)propane) prior to distillation. The mother liquor may, alternatively or additionally, be treated with ion-exchange resins and/or filtered. The mother liquor is distilled to remove bisphenol A, phenol, solvents, and other useful materials. After distillation, the remaining tarry residue is the mother liquor residue.

Exemplary distillation techniques include progressively (sequentially) higher vacuum/temperature conditions in order to separate the mother liquor into four fractions. For example, a first distillation column is operated under vacuum and temperature conditions to remove an overhead fraction containing relatively pure phenol (e.g. >97% purity). The bottoms of the first column are fed to a second distillation column. This second column operates under reduced pressures and elevated temperature conditions which remove a colored "light" fraction consisting mainly of residual isomers of bisphenol-A and Chroman along with other byproducts with known and unknown chemical structure. This lights fraction can be purged and discarded, or subjected to additional recovery by this or other processes. The bottoms of the second column are fed to a third column. The overheads of this third column typically contain 60-90% pure bisphenol-A depending on the temperature and pressure conditions used. The bottoms of the third column contain "heavies" or tars which is the mother liquor residue used in the recovery method described herein.

In another exemplary distillation technique the mother liquor is distilled in a vacuum distillation column and a portion of the bottom product can be recycled to the bisphenol reactor with the remainder fed to a second vacuum distillation column (phenol recovery column). The bottom product of this second vacuum distillation column is the mother liquor residue used in the recovery method described herein.

In a more general sense, the mother liquor is distilled with one of the end products being a mother liquor residue. The mother liquor residue is cracked with an aromatic sulfonic acid catalyst to form a cracked product mixture. Aromatic sulfonic acid catalysts are a well-known class of compounds as are methods of their preparation. Aromatic sulfonic acids may be represented by the general formula $RC_6H_4SO_3H$ in which R may be in any position in the phenyl ring wherein R represents hydrocarbyl having 1 to 25 carbon atoms, inclusive. Exemplary aromatic sulfonic acids include p-toluenesulfonic acid and dodecylbenzene sulfonic acid The term "hydrocarbyl" as used herein means the monovalent moiety obtained upon removal of a hydrogen atom from a parent hydrocarbon. Representative of hydrocarbyl is alkyl of 1 to 25 carbon atoms, inclusive, such as methyl, ethyl, propyl, butyl, pentyl, hexyl, heptyl, octyl, nonyl, undecyl, clecyl, dodecyl, octadecyl, nonodecyl, eicosyl, heneicysyl, docosyl, tncosyl, tetracosyl, pentacosyl and the isomeric forms thereof; aryl of 6 to 25 carbon atoms, inclusive, such as a phenyl, tolyl, xylyl, napthyl, biphenyl, tetraphenyl and the like; aralkyl of 7 to 25 carbon atoms, inclusive, such as benzyl, phenethyl, phenpropyl, phenbutyl, phenhexyl, napthoctyl and the like; cycloalkyl of 3 to 8carbon atoms, inclusive, such ascyclopropyl, cyclobutyl, cyclopentyl, cyclohexyl, cycloheptyl, cyclooctyl and the like.

The aromatic sulfonic acid is present in amounts of 100 to 10,000 parts per million by weight (ppm) of mother liquor residue, more specifically, 1000 to 5000 ppm, more specifically 2100 to 2700 ppm, even more specifically 2300 to 2550 ppm. Cracking occurs at temperatures of 100° C. to 300° C., more specifically, 120° C. to 180° C., and even more specifically 135° C. to 165° C. Cracking can occur at a pressure of 150 to 250 millimeters (mm) Hg, more specifically, 175 to 225 mm Hg. The cracker tank/heat exchanger may contain one or more internal baffles and one or more overflow baffles.

The cracked product mixture is then distilled to recover phenol. Distillation can occur at temperatures of 68 to 202° C. The recovered phenol can be recycled back into the bisphenol A synthesis. The recovered phenol may further comprise mercaptans. Mercaptans are sometimes used a co-promoters in bisphenol A synthesis. Distillation can occur in a distillation column which is located after the cracker tank/heat exchanger.

An exemplary method is shown in FIG. 1 where stream 5 is the mother liquor, 104 is a mother liquor tank, 43 and 46 are distillation steps, 33 is a condenser (also referred to as a phenol receiver) and C is where the cracking step occurs. Stream 5 is a mother liquor which can comprise 75 to 85 weight percent phenol, 10 to 15 weight percent of a combination comprising bisphenol A, isomers of bisphenol A and other byproduct components. Stream 1 is the mother liquor residue that can comprise 70 to 80 weight percent bisphenol A and isomers of bisphenol A, 0.5 to 3 weight percent phenol, with the balance being other byproduct components. Stream 2 is a tarry mixture that can exhibit viscosities of 80 to 230 centipoise at 176° Celsius.

In a particular embodiment, a mother liquor comprising 80 weight percent phenol, 14.5 weight percent bisphenol A and bisphenol A isomers with the balance comprising other by-products feeds into a phenol distillation column that is equipped with Mellapak 125X in the top section and Mellapak 252Y in the bottom section as packing material. Such column is operated at a temperature of 80 to 99° Celsius at the bottom section. This column may operate with an overhead pressure of 100 to 150 mm Hg. The overheads stream enters a condenser and into a phenol receiver. The effluent stream from the phenol receiver is mainly pure phenol (~99%). A cracker is present at the bottom of the column. A bottoms stream flows through the cracker and the cracking catalyst, that is an aromatic sulfonic acid such as those described above, is added in the cracker. It is also contemplated that the cracking catalyst can be added to the stream entering the cracker. The cracker may comprise one or more internal baffles and one or more overflow baffles and can operate at 120 to 180° C., more specifically 135 to 165° C., and an outlet stream pressure of 150 to 250 mm Hg, more specifically 175 to 225 mm Hg. Greater than or equal to 50 weight percent of the total feed to the cracker can be converted to phenol.

Downstream from the cracker (also sometimes described as the cracker tank), a secondary phenol stripping column can be used to recover more phenol overheads which can be recycled to a mother liquor tank and as such, mixed with the mother liquor stream to be re-fed and purified in the above mentioned phenol distillation column.

The material generated in the cracker can flow to the secondary phenol column as a vapor feed while all liquid effluent from the cracker can also feed the same column. The vapor stream enters towards the top of the column while the liquid stream can enter in the suction line at the bottom.

The bottoms stream of the secondary phenol stripping column is tar to burn. The secondary phenol stripping column can be a packed one comprising Koch type packing. The temperature along the column's axial direction can be 120 to 180 ° C.

Embodiment 1: A process for recovery of materials from a mother liquor residue comprising cracking a mother liquor residue with an aromatic sulfonic acid catalyst to form a cracked product mixture and separating phenol from the cracked product mixture wherein the mother liquor residue results from distillation of a mother liquor resulting from bisphenol A synthesis and isolation.

Embodiment 2: The process of Embodiment 1, wherein separating phenol from the cracked product mixture occurs by adding the cracked product mixture to a distillation column which precedes it in the process.

Embodiment 3: The process of Embodiment 1, wherein separating phenol from the cracked product mixture occurs in a distillation column which follows it in the process.

Embodiment 4: The process of any of Embodiments 1 to 3, wherein the aromatic sulfonic acid catalyst comprises p-toluenesulfonic acid or dodecylbenzene sulfonic acid.

Embodiment 5: The process of any of Embodiments 1 to 4, wherein the aromatic sulfonic acid catalyst is present in an amount of 100 to 10,000 parts per million by weight (ppm) of mother liquor residue.

Embodiment 6: The process of any of Embodiments 1 to 5, wherein cracking occurs at a temperature of 100° C. to 300° C.

Embodiment 7: The process of any of Embodiments 1 to 6, wherein cracking occurs at a pressure of 150 to 250 millimeters (mm) Hg.

Embodiment 8: The process of any of Embodiments 1 to 7, wherein the mother liquor residue comprises 70 to 80 weight percent bisphenol A and isomers of bisphenol A and 0.5 to 3 weight percent phenol.

Embodiment 9: The process of any of Embodiments 1 to 8, wherein greater than 50 weight percent of mother liquor residue is converted to phenol.

The invention is further illustrated by the following non-limiting example.

EXAMPLE

In a laboratory scale experiment a 3-neck round flask was placed into a silicon oil bath. The silicon oil bath was situated on top of a hot plate stirrer. A thermocouple was inserted in the first port of the flask. Nitrogen was introduced in the second (middle) port, and a tube leading to another flask for distillates was connected to the last port. 50 grams of mother liquor residue was weighed and placed in the 3-neck flask and the flask was placed in the oil bath on top of the hot plate. The mother liquor residue contained 89 weight percent bisphenol A and bisphenol A isomers, 11 weight percent other by products and no phenol. The flask was heated and once the desired temperature was reached (93 to 177° C.) 2500 ppm of dodecylbenzene sulfonic acid was added using a syringe. After 30 minutes, the sample remaining in the flask was weighed (to determine mass balance), and the residue and the product collected in the second flask was analyzed by ICP. 54 weight percent of the crackable material present in the mother liquor residue (the bisphenol A and bisphenol A isomers) was converted to phenol.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

We claim:

1. A process for recovery of materials from a mother liquor residue comprising cracking the mother liquor residue with an aromatic sulfonic acid catalyst at a temperature of 100° C. to 300° C. and a pressure of 150 to 250 millimeters (mm) Hg to form a cracked product mixture, transferring the cracked product mixture to a distillation column and separating phenol from the cracked product mixture in the distillation column, wherein the mother liquor residue results from distillation of a mother liquor resulting from bisphenol A synthesis and isolation.

2. The process of claim 1, wherein transferring the cracked product mixture to a distillation column comprises recycling the cracked product mixture to a distillation column which precedes the location used to perform cracking.

3. The process of claim 1, wherein the distillation column is located after the location used to perform the cracking.

4. The process of claim 1, wherein the aromatic sulfonic acid catalyst comprises p-toluenesulfonic acid or dodecylbenzene sulfonic acid.

5. The process of claim 1, wherein the aromatic sulfonic acid catalyst is present in an amount of 100 to 10,000 parts per million by weight (ppm) of mother liquor residue.

6. The process of claim 1, wherein cracking occurs at a temperature of 120° to 180° C.

7. The process of claim 1, wherein cracking occurs at a pressure of 175 to 225 millimeters (mm) Hg.

8. The process of claim 1, wherein the mother liquor residue comprises 70 to 80 weight percent bisphenol A and isomers of bisphenol A and 0.5 to 3 weight percent phenol.

9. The process of claim 1, wherein greater than 50 weight percent of mother liquor residue is converted to phenol.

10. A process for recovery of materials from a mother liquor residue comprising cracking the mother liquor residue with an aromatic sulfonic acid catalyst at a temperature of 100° C. to 300° C. and a pressure of 150 to 250 millimeters (mm) Hg to form a cracked product mixture, transferring the cracked product mixture to a distillation column and separating phenol from the cracked product mixture in the distillation column wherein the mother liquor residue comprises 70 to 80 weight percent bisphenol A and isomers of bisphenol A and 0.5 to 3 weight percent phenol and results from distillation of a mother liquor resulting from bisphenol A synthesis and isolation and further wherein greater than 50 weight percent of mother liquor residue is converted to phenol.

11. A process for making bisphenol A comprising cracking a mother liquor residue with an aromatic sulfonic acid catalyst at a temperature of 100° C. to 300° C. and a pressure of 150 to 250 millimeters (mm) Hg to form a cracked product mixture; transferring the cracked product mixture to a phenol stripping column, separating phenol from the cracked product mixture in the stripping column; reacting the phenol with acetone in the presence of an acid catalyst to form bisphenol A; and isolating the bisphenol A wherein the mother liquor residue results from distillation of a mother liquor resulting from bisphenol A synthesis and isolation.

12. The process of claim 11, wherein the phenol is added to the mother liquor and distilled prior to reacting with acetone.

13. The process of claim 1, wherein distillation occurs at a temperature of 68 to 202° C.

* * * * *